(12) United States Patent
Ogasawara et al.

(10) Patent No.: US 6,313,353 B1
(45) Date of Patent: Nov. 6, 2001

(54) METHOD FOR PRODUCING AN OPTICALLY ACTIVE ACYLOIN

(75) Inventors: Kunio Ogasawara; Takahiko Taniguchi, both of Sendai (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/154,249

(22) Filed: Sep. 16, 1998

(30) Foreign Application Priority Data

Sep. 26, 1997 (JP) .................................................... 9-279769

(51) Int. Cl.$^7$ .................................................... C07C 45/00
(52) U.S. Cl. ............................ 568/361; 568/367; 568/373
(58) Field of Search .................................... 568/338, 361, 568/367, 373; 566/108

(56) References Cited

PUBLICATIONS

CA:66:51800 abs of Zh. Obsch. Khim 36 (10) pp 1822, 1966.*

CA:83:113741 abs of Synthesis by Kirsme , (3) pp. 173–4, 1975.*

Journal of Amer Chem Soc by Paquette et al vol. 97 No. 5 pp 1101–1112, Mar. 1975.*

CA:82:16347 abs of J Org Chem by Vedejs 39(25) p 3641–3644, 1974.*

Yanagisawa et al., "Asymmetric Protonations of Enol Derivatives", pp. 411–420, (1997) Journal —Synlett (5).

* cited by examiner

*Primary Examiner*—Jean F Vollano
(74) *Attorney, Agent, or Firm*—Browdy and Neimark, P.L.L.C.

(57) ABSTRACT

By treating the reactant of 3,4-ditrimethylsilyloxytricyclo [4.2.1.0$^{2.5}$]nona-3,7-diene and binaphthol monoether-tin tetrachloride complex, optically active acyloin is produced. Using the optically active acyloin compound as a starting material, optically active oxydicyclopentadiene useful as several kinds of intermediates can be obtained efficiently.

3 Claims, No Drawings

METHOD FOR PRODUCING AN OPTICALLY ACTIVE ACYLOIN

BACKGROUND OF THE INVENTION

1. Field of the Invention

The present invention relates to a method for producing optically active acyloin compounds, which are useful for intermediates of medicines and the like, a binaphthol monoether complex using for the method, and a method for producing the complex.

2. Description of the Prior Art

Optically active acyloin compounds can be used as raw materials of optically active oxodicyclopentadiene, which are useful as starting materials of physiologically active materials such as pharmaceuticals (Japanese Patent Application No. 9-213840). For example, it is known that such compounds are starting materials of Aphanophine having analgetic effect. (J. Chem. Soc. Chem. Commun., 290 (1990)).

However, the method for producing optically active acyloin compounds is not known except a method using optical resolution (Japanese Patent Application 9-213840).

Although monomethyl ether of binaphthol monoether-tin tetrachloride complex is used for asymmetric hydrogenation of prochiral silyl enol ether by Yamamoto et al., there is no example that the complex is utilized for the compound represented by formula (1).

Hitherto, a method for producing the binaphthol monoether has been inefficient, because the useless isomer of ether products should be decomposed and removed by obtaining a derivative of a diastereomer as described by Tada et al. (J. Chem. Soc., Perk in Trans. 2, 1997) or by Salbadori et al. (Tetrahedron, 1987, 43, 4969) or by using HPLC as described by Park et al. (J. Org. Chem., 1982, 47, 4037).

As described above, as a method for producing optically active acyloin compounds, a method using optical resolution is known. The optical resolution method is effective when both enantiomers are required, but the method is ineffective when either one of the enantiomers is needed.

DISCLOSURE OF THE INVENTION

The present inventors earnestly have studied a method for producing only one of the enantiomers of optically active acyloin compounds to solve the said problems, in result, they have found a method for producing the optically active acyloin compound represented by formula (3-1) or (3-2), characterized in that 3,4-bistrimethylsilyloxy tricyclo [4.2.1.0$^{2,5}$] nona-3,7-diene represented by formula (1):

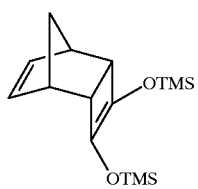

(1)

wherein TMS indicates trimethylsilyl, is used as a starting material, the diene is reacted with binaphthol monoether-tin tetrachloride complex represented by either of general formulas (2-1) and (2-2):

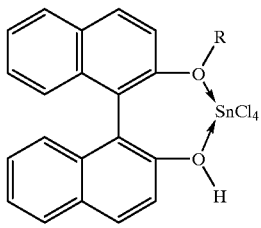

(2-1)

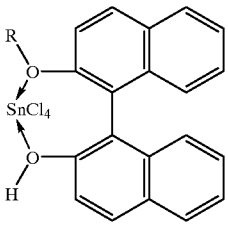

(2-2)

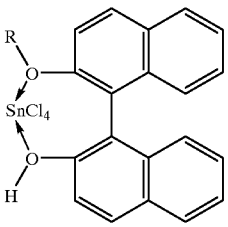

(2-2)

wherein R indicates straight or branched alkyl or alkenyl, or aralkyl, aryl or benzyloxyalkyl to obtain either of compounds represented by either of formulas (3-1) and (3-2):

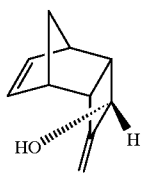

(3-1)

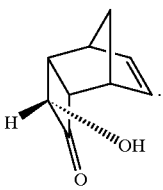

(3-2)

Moreover, they have found that only desired isomer of binaphthol monoether, which is a stating material of binaphthol monoether-tin tetrachloride complex, can be obtained by reacting a corresponding alcohol with binaphthol by Mitsunobu reaction.

Further, they have also found a new method for producing binaphthol monoether-tin tetrachloride complex represented by formula (2).

It is apparent from the said description that the present invention aims to provide a new method for producing optically active acyloin compound represented by formula (3-1) or (3-2) and a new method for producing binaphtholmonoether-tin tetrachloride complex represented by the above formula (2-1) or (2-2), which is used in the above method. The other objects are explained in the following description.

The present invention has the following constitutions of (1) to (7).

(1) A method for producing an optically active acyloin represented by either of formula (3-1) and (3-2) comprising using as a starting material 3,4-bistrimethylsilyloxytricyclo [4.2.1.0$^{2.5}$] nona- 3,7-diene represented by formula (1):

(1)

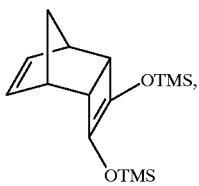

wherein TMS indicates trimethylsilyl, reacting the diene with binaphthol monoether-tin tetrachloride complex represented by either of general formula (2-1) and (2-2):

(2-1)

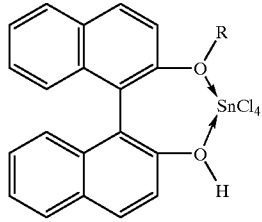

(2-2)

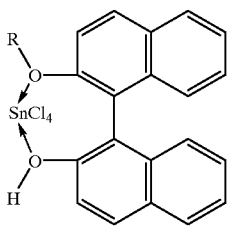

(2-2)

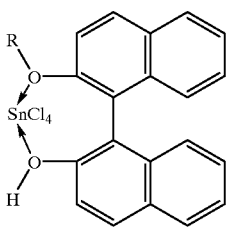

wherein R indicates straight or branched alkyl or alkenyl, or aralkyl, aryl or benzyloxyalkyl, and obtaining either of compounds represented by formula (3-1) or (3-2):

(3-1)

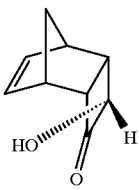

(3-2)

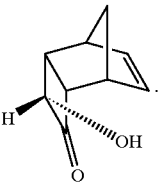

(2) A method for producing an optically active acyloin in the above (1), wherein R is isopropyl in general formulas (2-1) and (2-2).

(3) A method for producing an optically active acyloin in the above (1), wherein R is 2,6-dimethylhept-4-yl in general formulas (2-1) and (2-2).

(4) Binaphthol monoether-tin tetrachloride complex represented by general formula (2-1) or (2-2):

(2-1)

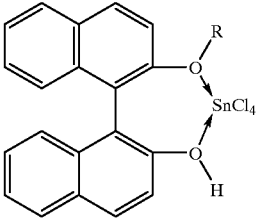

(2-2)

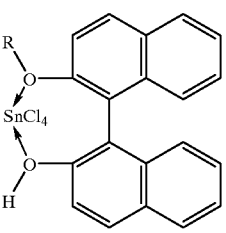

(2-2)

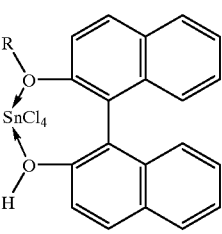

wherein R indicates isopropyl, 2,6-dimethylhept-4-yl, alkenyl, aralkyl, aryl or benzyloxyalkyl.

(5) Binaphthol monoether-tin tetrachloride complex in the above (4), wherein R is either of groups selected from isopropyl and 2,6-dimethylhept-4-yl.

(6) A method for producing a binaphthol monoether-tin tetrachloride complex represented by either of general formulas (2-1) and (2-2):

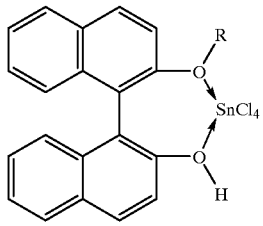
(2-1)

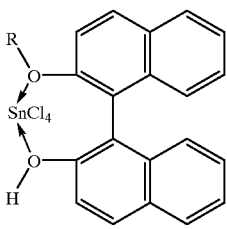
(2-2)

wherein R indicates isopropyl, 2,6-dimethylhept-4-yl, alkenyl, or aralkyl, aryl, or benzyloxyethtyl, comprising reacting optically active binaphthol represented by either of formulas (4-1) and (4-2)

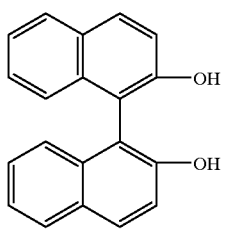
(4-1)

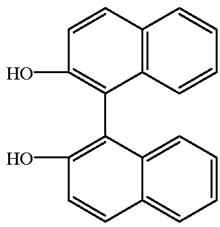
(4-2)

with an alcohol represented by formula (5)

$$R—OH \qquad (5)$$

wherein R indicates isopropyl, 2,6-dimethylhept-4-yl, alkenyl, or aralkyl, aryl, or benzyloxyethtyl, in the presence of triphenylphosphin by adding azodicarboxylic acid diester, obtaining binaphthol monoether represented by either of general formulas (6-1) and (6-2):

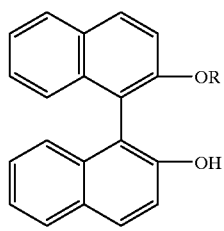
(6-1)

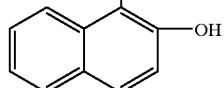
(6-2)

and reacting this compound with tin tetrachloride to obtain the above binaphthol monoether-tin chloride.

(7) Binaphthol monoether represented by general formula (6-1) or (6-2):

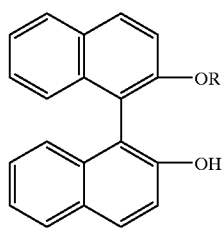
(6-1)

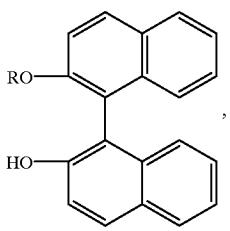

wherein R indicates isopropyl, 2,6-dimethylhept-4-yl, alkenyl, aralkyl, aryl or benzyloxyethyl.

The method for producing optically active acyloin compound of the present invention is represented by the following reaction formula. For convenience sake, it is described by using a (−)-compound.

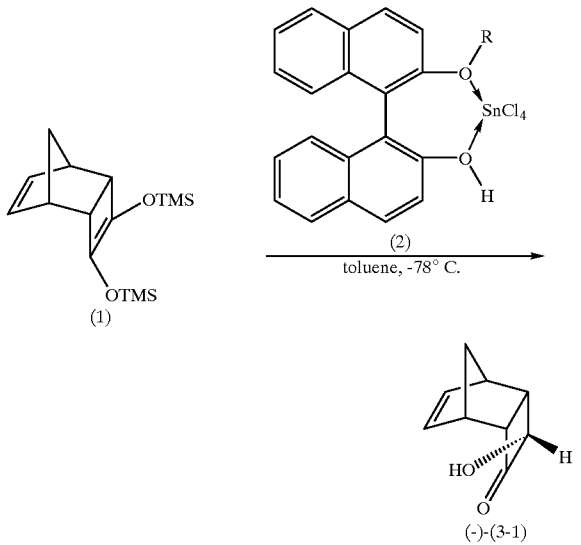

Compound (1) of the starting material can be easily obtained by a Millor's method, namely, by reacting cis-5-norbornen-endo-2,3-dicarboxylic acid with trimethylsilyl chloride in the presence of sodium (J.Org. Chem., 41, 1221 (1976)).

Compound (2) can be obtained by adding dropwise azodicarbxylic acid diester into a mixture solution of commercially available optically active binaphthol, alcohol and triphenylphosphine, stirring at room temperature of 10° C.–40° C., and obtaining the monoether represented by general formula (6). As a reaction solvent, diethyl ether, diisoprpyl ether, THF, chloroform, methylene chloride, or dichloroethane, preferably THF, can be used. The product is purified by silica gel chromatography, or recrystallization to obtain pure monoether (formula (4-1) or (4-2)). Then, the monoether and tin tetrachloride in a solution are mixed at room temperature of 10° C.–40° C. to obtain compound (2).

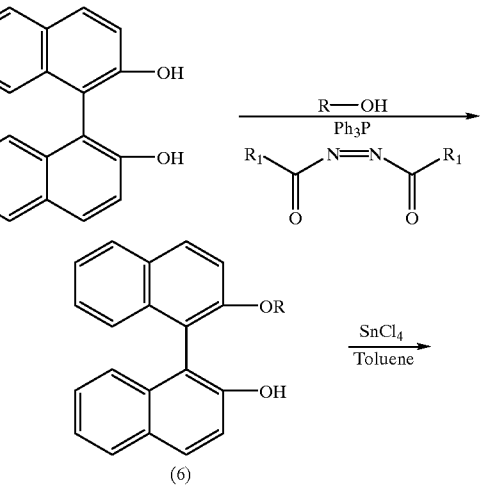

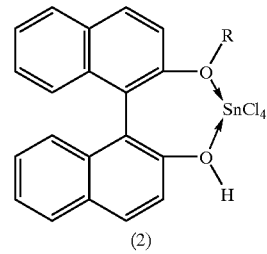

wherein $R_1$ is alkyl such as ethyl, isopropyl or cyclohexyl.

The following describes a method for producing an optically active acyloin compound.

A toluene solution of compound (2) is cooled to −60° C. to −80° C. Then, the compound (1) is slowly added while the temperature is maintained at a temperature of −60° C. to −80° C. The ratio of compound (2) to compound (1) is 1/100 to 1.5 times, preferably 1.2 times. After the solution is stirred for 10 minutes to 10 hours, preferably 2 hours, a 10% HCl aqueous solution is added and stirred, and the solution is diluted with organic solvent such as ethyl ether, isopropyl ether or t-butylmethyl ether, and the separated organic layer is washed with a saturated NaCl aqueous solution. The organic layer is then dried and the solvent is distilled off under reduced pressure. The resulting residue is purified by silica gel chromatography and objective compound (3) can be obtained.

By using the production method of the present invention, useful intermediates represented by formula (3) can be produced, and from these compounds, optically active oxo-cyclopentadiene which is a starting material of several kinds of physiologically active materials can be obtained. In addition, binaphthol monoether has been obtained by ineffective methods. By the method of the present invention, only the stereoisomer can be effectively produced.

DESCRIPTION OF THE PREFERRED EMBODIMENTS

The following examples are intended to further illustrate the present invention and not to limit the invention by these examples.

The optical purity, which is described in the following, is determined by HPLC analysis using a CHIRALCEL OD column manufactured by Daicel Company (elution: 0.5–10% isopropanol-hexane).

EXAMPLE 1

Synthesis of (S)-binaphthol monoisopropyl ether (S)-binaphthol (99% ee, 1.43 g, 5 mmol), triphenylphosphine (1.32 g, 5 mmol) and isopropanol (3 ml) were dissolved in THF (50 ml). To the solution, diethylazodicarboxylate (40% toluene solution, 2.2 ml, 5 mmol) was added dropwise at room temperature. After stirring at room temperature for 24 hours, the reaction mixture was concentrated under reduced pressure, the residue was treated by silica gel chromatography (80 g, developing solvent: hexane/ethyl acetate=8/1), and (S)-binaphthol monoisopropyl ether (98.5 mg, yield 6%, 98.5% ee) was obtained. The optical rotation was $[\alpha]_D^{24}$+81.8° (c0.9, CHCl$_3$)

EXAMPLE 2

Synthesis of (S)-binaphthyl mono-2,6-dimethylhept-4-yl ether (S)-binaphthol (99% ee, 1.43 g, 5 mmol), triphenylphosphine (1.71 g, 6.5 mmol) and 2,6-dimethylhepta-4-ol (1.08 g, 7.5 mmol) were dissolved in THF (50 ml). To the solution, diethylazodicarboxylate (40% toluene solution, 2.85 ml, 6.5 mmol) was added dropwise at room temperature. After stirring at room temperature for 18 hours, the reaction mixture was concentrated under reduced pressure, the residue was treated by silica gel chromatography (80 g, developing solvent: hexane/ethyl acetate=8/1), and (S)-binaphthyl mono-2,6-dimethylhept-4-yl ether (1.37 g, yield 66%, 99% ee) was obtained. The values of physical properties were as follows.

$[\alpha]_D^{29}$+31.70° (c1.502, CHCl$_3$)

IR (nujor, cm$^{-1}$) 3540, 3442

H NMR (300 MHz, CDCl$_3$) d 8.00 (d, J=9.1 Hz, 1H), 7.91–7.81 (m, 3H), 7.46–7.13 (m, 7H), 7.05 (brd, J=7.4 Hz, 1H), 4.99 (s, 1H), 4.37 (q, J=6.6 Hz, 1H), 1.62–0.66 (m, 6H), 0.80 (d, J=6.6 Hz, 3H), 0.7.9 (d, J=6.6 Hz, 3H), 0.60 (d, J=6.3 Hz, 3H), 0.59 (d, J=6.6 Hz, 3H).

Using the same method, the other monoether compounds were synthesized. The physical properties are shown in Table 1 (Examples 3–10).

TABLE 1

| Examples | Constitutional formula | Values of physical properties |
|---|---|---|
| 3 | binaphthyl with OH and OMe | mp. 89~91° C. <br> $[\alpha]_D^{28}$ + 44.8° (c 1.4, CHCl$_3$) |
| 4 | binaphthyl with OH and OEt | mp. 79~82° C. <br> $[\alpha]_D^{27}$ + 43.7° (c 1.2, CHCl$_3$) |
| 5 | binaphthyl with OH and O-CH$_2$CH$_2$-OBn | $[\alpha]_D^{29}$ + 12.0° (c 0.8, CHCl$_3$) |
| 6 | binaphthyl with OH and O-(CH$_2$)$_3$-OBn | $[\alpha]_D^{27}$ + 20.3° (c 1.9, CHCl$_3$) |

TABLE 1-continued

| Examples | Constitutional formula | Values of physical properties |
|---|---|---|
| 7 | 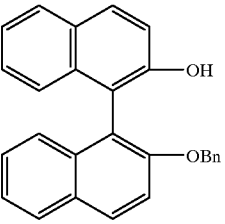 | mp. 120.5~121.5° C.<br>$[\alpha]_D^{30}$ + 2.8° (c 1.2, CHCl$_3$) |
| 8 | 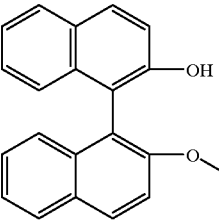 | $[\alpha]_D^{27}$ + 39.5° (c 1.0, CHCl$_3$) |
| 9 | 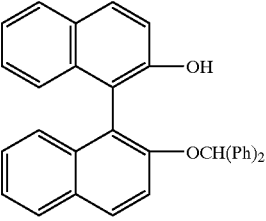 | $[\alpha]_D^{27}$ + 13.1° (c 1.0, CHCl$_3$) |
| 10 | 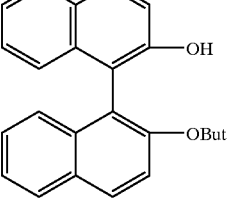 | $[\alpha]_D^{28}$ + 249.5° (c 0.3, CHCl$_3$) |

These monoether compounds also can be mixed with tin tetrachloride by the method described in the following Example 3 to obtain binaphthol monoether-tin tetrachloride complex.

EXAMPLE 11

Synthesis of an acyloin compound (1)

Tin tetrachloride solution (0.44 ml, 0.44 mmol, a 1.0 M dichloromethane solution) was added to a solution of (S)-binaphtholmono 2,6-dimethylhepta-4-yl ether (181 mg, 0.44 mmol, 99% ee), which is obtained in Example 2, in anhydrous toluene (5 ml) solution under argon atmosphere at room temperature and the mixture was stirred for 1 hour. The reaction solution was cooled to −780° C., compound (1) (108 mg, 0.37 mmol) in a solution of anhydrous toluene (1 ml) was added dropwise for 10 minutes, and the mixture was stirred for 2 hours at the same temperature. After the reaction, an aqueous solution of 10% HCl (2 ml) was added and stirred for 10 minutes, the solution was diluted with ethyl ether, and the separated organic layer was washed with a saturated NaCl aqueous solution. Then, the organic layer was dried over anhydrous magnesium sulfate and the solvent was distilled off under reduced pressure. The resulting residue was treated by silica gel chromatography (elution solvent: Et$_2$O/hexane=1/1 vol/vol), and colorless solid (−)-acyloin compound (2) (45 mg, 82%) and (S)-binaphthylmono 2,6-dimethylhept-4-yl ether (178 mg, collected by 98%) were obtained from the elution parts.

In addition, (−)-acyloin compound (2) was 94% ee (CHIRALCEL OD, 5% iPrOH/hexane). The physical properties were as follows: $[\alpha]_D^{24}$ −204.3° (c1.0, CHCl$_3$), m.p. 104–106° C. (Et$_2$O/hexane); IR (nujor, cm$^{-1}$) 3376, 1761; $^1$H NMR (300 MHz, CDCl$_3$) d 6.19 (dd, J=5.8, 3.0 Hz, 1H), 6.13 (dd, J=5.8, 2.5 Hz, 1 H), 4.43 (m, 1H), 3.57 (m, 1H), 3.09 (m, 1H), 2.07 (d, J=8.0 Hz, 1H), 1.77 (d, J=8.2 Hz, 1H), 1.54 (d, J=8.2 Hz, 1H); HRMS m/z C$_9$H$_{10}$O$_2$ (M+) calcd. 150.0680, obsd. 150.0676.

The collected (S)-binaphthylmono 2,6-dimethylhepta-4-yl ether was 99% ee (CHIRALCEL OD, 2% iPrOH/hexane).

EXAMPLE 12

Synthesis of an acyloin compound (2)

Tin tetrachloride (0.44 ml, 0.44 mmol, a 1.0 M dichloromethane solution) solution was added to a solution of (S)-binaphthylmono isopropyl ether (98.5 mg, yield 6%, 98.5% ee) obtained in Example 1, as a substitute for (S)-binaphthylmono 2,6-dimethylhept-4-yl ether obtained in Example 2, in anhydrous toluene (5 ml) solution under argon atmosphere at room temperature and the mixture was stirred for 1 hour. The reaction solution was cooled to −780° C., compound (1) (108 mg, 0.37 mmol) in a solution of anhydrous toluene (1 ml) was added dropwise for 10 minutes, and the mixture was stirred for 2 hours at the same temperature. After the reaction, an aqueous solution of 10% HCl (2 ml) was added and stirred for 10 minutes, the solution was diluted with ethyl ether, and the separated organic layer was washed with a saturated NaCl aqueous solution. Then, the organic layer was dried over anhydrous magnesium sulfate and the solvent was distilled off under reduced pressure. The resulting residue was treated by silica gel chromatography (elution solvent: Et$_2$O/hexane=1/1 vol/vol), and colorless solid (−)-acyloin compound (2) (48 mg, 82%) and (S)-binaphthylmonoisopropyl ether (collected by 98%) were obtained from the elution parts.

In addition, (−)-acyloin compound (2) was 90% ee (CHIRALCEL OD, 5% iPrOH/hexane), and each physical property of the compound agreed very closely with those in Example 3.

Moreover, collected (S)-binaphthyl monoisopropyl ether was 99% ee (CHIRALCEL OD, 2% iPrOH/hexane).

What is claimed is:

1. A method for producing an optically active acyloin, comprising using as a starting material 3,4-bistrimethylsilyloxytricyclo[4.2.1.0$^{2.5}$]nona-3,7-diene represented by formula (1):

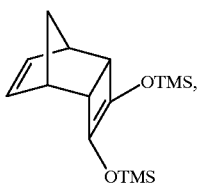

(1)

wherein TMS indicates trimethylsilyl, reacting the diene with binaphthol monoether-tin tetrachloride complex represented by either of general formulas (2-1) and (2-2):

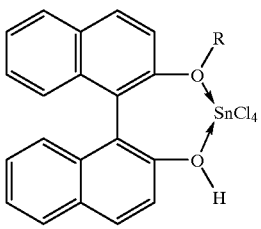

(2-1)

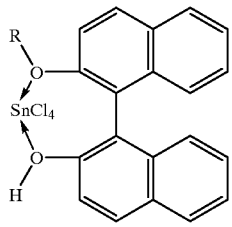

(2-2)

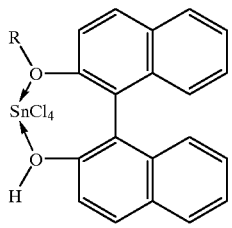

(2-2)

wherein R indicates straight or branched alkyl or alkenyl, or aralkyl, aryl or benzyloxyalkyl, and obtaining either of compounds represented by either of formulas (3-1) and (3-2):

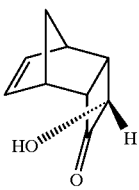

(3-1)

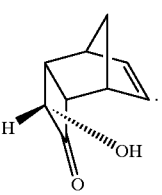

(3-2)

2. A method for producing an optically active acyloin claimed in claim 1, wherein R is isopropyl in general formulas (2-1) and (2-2).

3. A method for producing an optically active acyloin claimed in claim 1, wherein R is 2,6-dimethylhept-4-yl in general formulas (2-1) and (2-2).

* * * * *